(12) United States Patent  
Kidane et al.

(10) Patent No.: US 8,362,773 B2
(45) Date of Patent: Jan. 29, 2013

(54) SYSTEM AND METHOD FOR MODELING GRADIENT COIL OPERATION INDUCED MAGNETIC FIELD DRIFT

(75) Inventors: Tesfaye Kebede Kidane, Florence, SC (US); Timothy John Havens, Florence, SC (US); Longzhi Jiang, Florence, SC (US); Mark Haig Khachaturian, Florence, SC (US); Zhenyu Zhang, Florence, SC (US)

(73) Assignee: General Electric Company, Schenectady, NY (US)

( * ) Notice: Subject to any disclaimer, the term of this patent is extended or adjusted under 35 U.S.C. 154(b) by 351 days.

(21) Appl. No.: 12/897,831

(22) Filed: Oct. 5, 2010

(65) Prior Publication Data

US 2012/0082357 A1    Apr. 5, 2012

(51) Int. Cl.
*G01V 3/00* (2006.01)
(52) U.S. Cl. .................................. 324/312; 324/314
(58) Field of Classification Search .................. 324/312, 324/314, 318, 322
See application file for complete search history.

(56) References Cited

U.S. PATENT DOCUMENTS

| 6,456,073 B2 * | 9/2002 | Uetake et al. ............... 324/309 |
| 6,552,539 B2 * | 4/2003 | Uetake ....................... 324/307 |
| 7,141,974 B2 | 11/2006 | Edelstein et al. |
| 7,375,526 B2 | 5/2008 | Edelstein et al. |
| 8,154,294 B2 * | 4/2012 | Takizawa et al. ........... 324/318 |

* cited by examiner

*Primary Examiner* — Louis Arana
(74) *Attorney, Agent, or Firm* — Ziolkowski Patent Solutions Group, SC (57) ABSTRACT

A system and method for modeling gradient coil operation induced magnetic field drift include a computer programmed to acquire a pulse sequence to be applied during an MR scan and determine a power spectrum of a plurality of gradient pulses of the pulse sequence. The computer is also programmed to calculate a drift of the magnetic field attributable to application of the plurality of gradient pulses by the plurality of gradient coils during application of the pulse sequence and apply the pulse sequence during the MR scan. The computer is further programmed to acquire MR data based on application of the pulse sequence, correct the acquired MR data based on the calculated drift of the magnetic field, and reconstruct an image based on the corrected MR data.

22 Claims, 6 Drawing Sheets

SYSTEM AND METHOD FOR MODELING GRADIENT COIL OPERATION INDUCED MAGNETIC FIELD DRIFT

BACKGROUND OF THE INVENTION

Embodiments of the invention relate generally to MR imaging and, more particularly, to a system and method for modeling gradient coil operation induced magnetic field and/or harmonics drift.

In MRI and NMR systems, a number of coils carry an electric current to generate a high strength, relatively homogeneous magnetic field. This field may be referred to the main field or $B_0$ field. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals is digitized and processed to reconstruct the image using one of many well known reconstruction techniques.

Rather than being homogenous, the gradient fields ($G_x$, $G_y$, and $G_z$) vary in magnitude along each respective axis. In cylindrical magnet systems, the coils generating the main field are axially aligned. Typically, gradient coils are arranged in a tubular space radially inside of the main field coils. In typical arrangements, the gradient coils comprise resistive wire embedded in a potted material such as a resin.

Passive shimming arrangements commonly employ shim trays that are housed within slots formed in the potting material of the gradient coils, in directions parallel to the magnet axis. The shim trays include a number of pockets along their length. Shim pieces, typically flat square or rectangular pieces of steel, are places within the pocket, and then the shim tray is loaded into the gradient coils.

The operation of the gradient coils commonly involves a series of fast "on-off" switches depending on the pulse sequence is used. It has been observed that the gradient operation can cause $B_0$ field drift and harmonics drift during operation, and image quality can be compromised as a result. Such gradient operation is particularly detrimental to fully passive shimming magnets where large amount of steel shims are used to maintain homogeneity.

Figure 1:
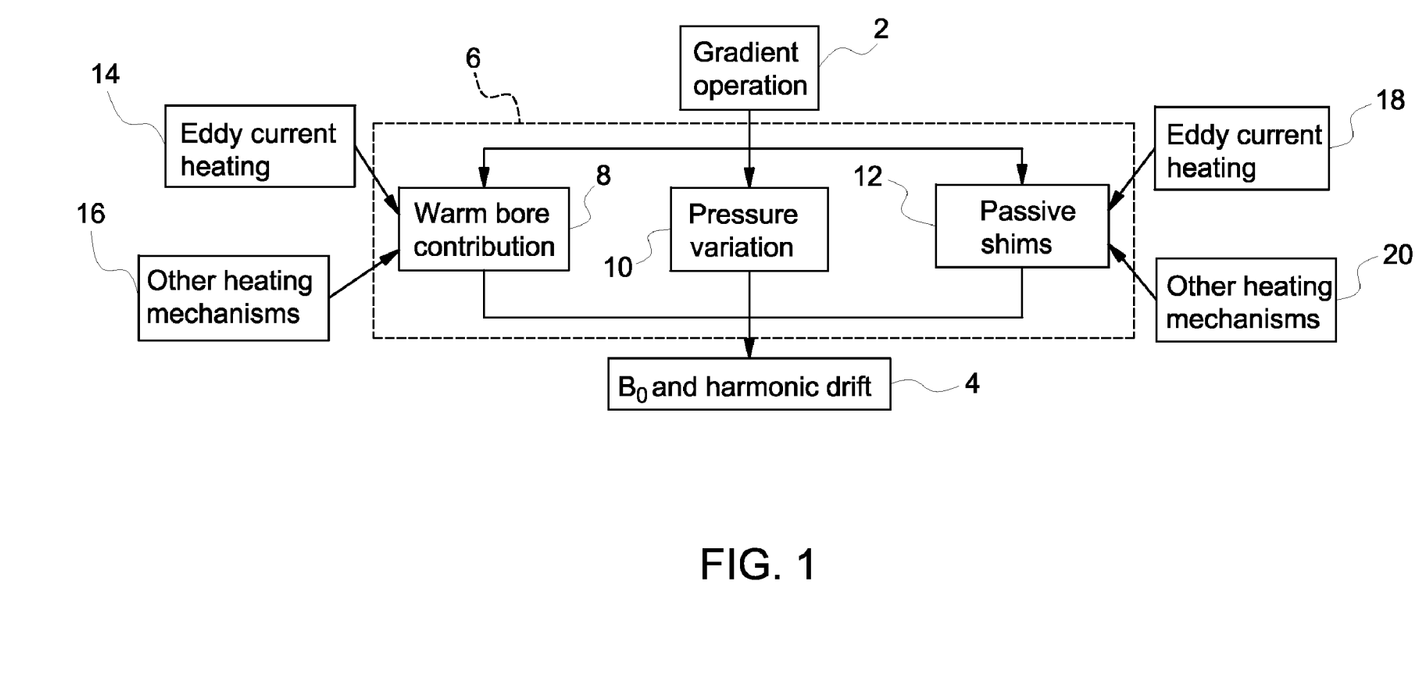
FIG. 1 is a block diagram correlating gradient operation with magnetic field drift and harmonic drift.

The $B_0$ drift and harmonic drift caused by operations of the gradient coils have complex dependence to various components in magnet systems via different mechanisms. FIG. 1 shows a block diagram correlating gradient operation with magnetic field drift and harmonic drift. A first block 2 represents gradient operation that occurs during an MR scan sequence. For example, gradient operation may occur in a spin echo MR sequence where the gradient coils of the MR system are powered according to a pulse sequence such that MR data may be acquired for a particular slice of a patient or scan object. Gradient operation 2 can lead to $B_0$ and harmonic drift 4 by way of a plurality of contributing factors 6 including a warm bore contribution 8, a contribution due to pressure variation 10, and a contribution due to passive shims 12 in an MR system. $B_0$ and harmonic drift 4 can lead to compromised image quality.

Warm bore contribution 8 can be caused, for example, by eddy current heating 14 and other heating mechanisms 16 such as convection and conduction. Pressure variation 10 can be caused, for example, by heat transfer by induced eddy currents from the gradient coils to the helium vessel, which increases pressure in the helium vessel. A temperature change in the helium in the helium vessel may also cause pressure variation 10 to change. Additionally, the passive shims 12 may affect $B_0$ and harmonic drift 4 due to eddy current heating 18 and other heating mechanisms 20.

Figure 2:
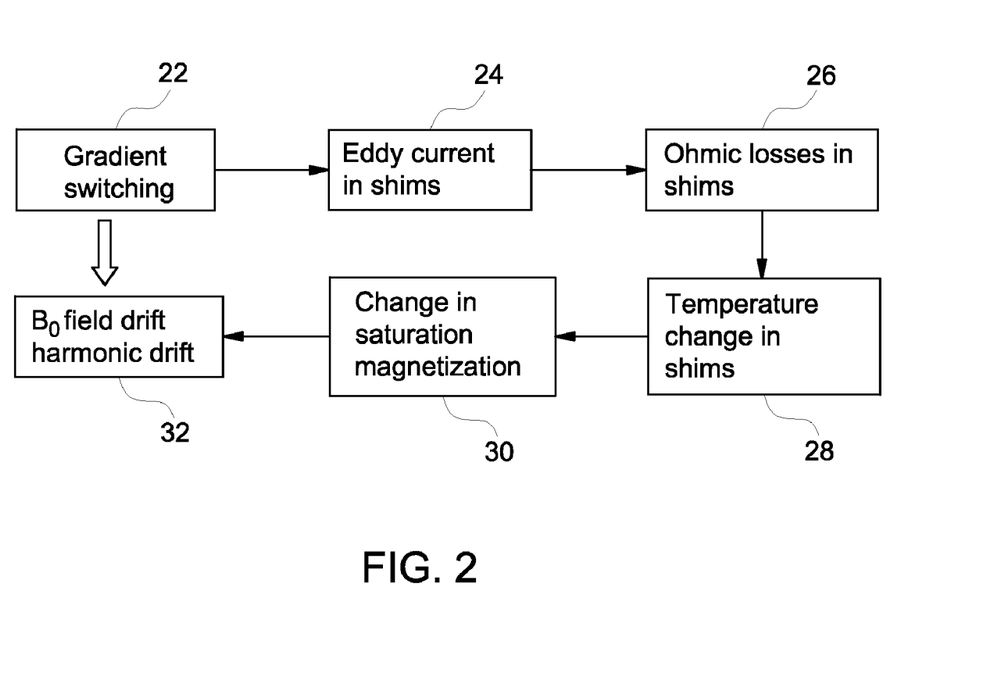
FIG. 2 is a block diagram showing a contribution to magnetic field drift and harmonic drift via passive shims.

FIG. 2 is a block diagram showing a contribution to magnetic field drift and harmonic drift via passive shims. The switching electromagnetic fields 22 generated by gradient coils can induce eddy current 24 into the steel, iron, or other ferromagnetic shims that results in Ohmic losses 26, which cause the temperature to rise in the shims 28. In addition the heat transfer from hot gradient surface and gradient cooling water will change the shim temperature and hence the shim magnetization. The shims are commonly magnetized to saturation along the easy axis by the main field and contribute to the $B_0$ field and harmonics in the field-of-view (FOV) as dipoles. The saturation magnetization of soft magnetic material is temperature dependent; therefore, the magnetic field produced by the shims is temperature dependent and can be changed 30. The change in saturation magnetization 30, which can be altered by operation of the gradient coils as shown, contributes to magnetic field drift and harmonic drift 32.

It would therefore be desirable to have a system and method capable of characterizing and compensating for magnetic field drift and/or harmonic drifts for MR imaging and image reconstruction.

BRIEF DESCRIPTION

In accordance with one aspect of the invention, a magnetic resonance imaging (MRI) apparatus comprises an MRI system and a computer. The MRI system comprises a magnet configured to generate a magnetic field, a plurality of gradient coils, and an RF transceiver system and an RF switch controlled by a pulse module to transmit RF signals to an RF coil assembly to acquire MR images. The computer is programmed to acquire a pulse sequence to be applied during an MR scan and determine a power spectrum of a plurality of gradient pulses of the pulse sequence. The computer is also programmed to calculate a drift of the magnetic field attributable to application of the plurality of gradient pulses by the plurality of gradient coils during application of the pulse sequence and apply the pulse sequence during the MR scan. The computer is further programmed to acquire MR data based on application of the pulse sequence, correct the acquired MR data based on the calculated drift of the magnetic field, and reconstruct an image based on the corrected MR data.

In accordance with another aspect of the invention, a method comprises determining a power spectrum of a plurality of gradient pulses to be applied in a pulse sequence during an MR scan, determining a magnetic field drift of a main magnetic field due to application of the plurality of gradient pulses during the pulse sequence, and applying the pulse sequence during the MR scan. The method also comprises acquiring MR data based on application of the pulse sequence, correcting the acquired MR data based on the magnetic field drift, and reconstructing an image based on the corrected MR data.

In accordance with another aspect of the invention, a non-transitory computer readable medium having stored thereon a computer program comprises instructions, which, when executed by a computer, cause the computer to determine a power spectrum of a plurality of gradient pulses to be applied in a pulse sequence during an MR scan and to characterize a dependency of a main magnetic field on at least one frequency of the power spectrum to obtain a main magnetic field drift. The instructions further cause the computer to apply the pulse sequence during the MR scan, acquire MR data based on application of the pulse sequence, correct the acquired MR data based on the main magnetic field drift, and reconstruct an image based on the corrected MR data.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Embodiments of the invention provide a system and method for characterizing and modeling gradient coil operation induced magnetic field drift and harmonics drift. Based on the model of the magnetic field drift and harmonics drift, real-time compensation thereof during MR scanning may be performed to increase image quality.

Characterizing gradient coil operation includes characterizing the $B_0$ and/or harmonics drift as a function of frequency. Once characterization of the $B_0$ and/or harmonics drift as a function of frequency is determined, the $B_0$ and/or harmonics drift due any PSD power spectrum PW(f) can be characterized by Eqn. 1. While embodiments of the invention described below may be directed to $B_0$ drift, one skilled in the art would recognize that harmonics drift may be substituted therefor.

The $B_0$ drift due to a given pulse sequence diagram (PSD) power spectrum (PW) is given, for each gradient axis, by:

$$B_0^{PSD}(f) = PW(f) \cdot B_0(f) \qquad \text{(Eqn. 1).}$$

In the time domain, Eqn. 1 becomes the convolution integral. The $B_0$ drift contribution for each PSD applied for an amount of time t is given by:

$$B_0^{PSD}(t) = \int_0^t PW(t-t')B_0(t')dt'. \qquad \text{(Eqn. 2)}$$

Sampling at a uniform time $\Delta t$, the convolution integral (Eqn. 2) can be approximated by the sum:

$$B_0^{PSD}(m\Delta t) = \sum_j PW(m\Delta t - t_j)B_0(t_j). \qquad \text{(Eqn. 3)}$$

The frequency dependency of $B_0$ can be broken down in to three major components: 1) a contribution due to passive shim pieces heating ($B_0^{shim}$), 2) a contribution due to warm bore (WB) heating ($B_0^{WB}$), and 3) a contribution due to pressure variation ($B_0^P$). An expression for the frequency dependency of $B_0$ is given by:

$$B_0(f) = B_0^{shim}(f) + B_0^{WB}(f) + B_0^P(f) \qquad \text{(Eqn. 4).}$$

Each component of $B_0(f)$ (i.e, $B_0^{shim}(f)$, $B_0^{WB}(f)$, and $B_0^P(0)$ can be characterized by determining the respective component from a physical model based analytical or numerical simulation or by experimental measurements.

A dominant contribution to $B_0$ drift from shim pieces is due to the change in magnetization as a result of temperature change. The following discussion shows analytically determining $B_0$ drift due to eddy current on shim pieces according to an embodiment of the invention.

Suppose $A(r_i)$ is the magnetic vector potential due to the gradient at the location of the ith shim piece. Then, $$A(r_i, z_i, t) = A(r_i, z_i)e^{j\omega t} \qquad \text{(Eqn. 5).}$$

The joule heating on the ith piece with conductivity a is given by:

$$P(r_i, z_i) = \vec{J}(r_i, z_i) \cdot \vec{E}(r_i, z_i) \qquad \text{(Eqn. 6),}$$

Since $$\vec{J}(r_i, z_i) = \sigma \vec{E}(r_i, z_i) \qquad \text{(Eqn. 7),}$$

Eqn. 6 may be rewritten as:

$$P(r_i, z_i) = \sigma E(r_i, z_i)^2 \qquad \text{(Eqn. 8).}$$

From Maxwell's equation, the electric field due to a time varying magnetic field is given by:

$$E(r_i, z_i) = -\frac{\partial A(r_i, z_i, t)}{\partial t}. \qquad \text{(Eqn. 9)}$$

Hence, $$P(r_i, z_i) = \sigma A(r_i, z_i)^2 \omega^2 \qquad \text{(Eqn. 10).}$$

Accordingly, the total energy dissipated on the shim surface may be represented as:

$$P_T = \int_S P(r_i, z_i)ds. \qquad \text{(Eqn. 11)}$$

Once the power dissipation in the shim pieces is calculated as a function of frequency using Eqn. 11, the temperature rise in the shim pieces can be determined by:

$$T(r_i) = \frac{P(r_i)}{c(T)}, \quad \text{(Eqn. 12)}$$

where c(T) is the specific heat capacity of the shim piece material. For temperatures well below Curie temperature ($T_c$), the temperature dependence is known for saturated magnetization. Hence, the magnetic field (B0) due to a the ith shim piece is $$B_0(r_i, z_i, T) = \frac{\mu_0 m_z(T)}{4\pi}\left(\frac{3z_i^2}{(r_i^2+z_i^2)^{5/2}} - \frac{1}{(r_i^2+z_i^2)^{3/2}}\right), \quad \text{(Eqn. 13)}$$

where:

$$m_z(T) = m_0(1-\alpha T^{3/2}) \quad \text{(Eqn. 14)},$$

and where $m_0$ is magnetization at 300 Kelvin.

The $B_0$ drift due to change in magnetization in shim pieces due to eddy current heating may be thus shown to vary as frequency square:

$$B_0^{eddy} \propto \omega^2 \quad \text{(Eqn. 15)}.$$

According to another embodiment of the invention, the $B_0$ drift due to change in magnetization in shim pieces may be measured together with temperature changes in the shim pieces. In this manner, the $B_0$ drift due to change in magnetization in shim pieces due to all mechanism of heat transfer may be determined through measurement accurately.

A dominant contribution to $B_0$ drift due to WB is mainly caused by the change in permeability with temperature as a result of eddy current heating. This permeability change results in additional uncompensated B0 term and change in magnetization of the warm bore. The following discussion shows analytically determining $B_0$ drift due to WB according to an embodiment of the invention due to eddy current heating.

Suppose A(R,z) is the vector potential due the gradient at the location (R,z) on the surface of the WB. Then, $$A(R,z,t) = A(R,z)e^{j\omega t} \quad \text{(Eqn. 16)}.$$

Following a similar line of reasoning as that described above regarding $B_0$ drift due to eddy current on the shim pieces, the eddy current induced on the surface of the WB and hence the $B_0$ field produced by the eddy current as a result of heating and field generation can be expressed as:

$$B_0^{WB} \propto \omega^2 + \omega \quad \text{(Eqn. 17)}.$$

According to another embodiment of the invention, the $B_0$ drift due to WB caused by all mechanisms of heat transfer may be measured together with temperature changes in the warm bore. In this manner, the $B_0$ drift due to WB may be determined through measurement.

The $B_0$ drift due to pressure change may be determined by measurement according to an embodiment of the invention. For example, the $B_0$ drift may be measured at different pressures such as by changing the pressure in the steps of, for example, 0.5 psi and measuring the resulting $B_0$ drift. Other pressure intervals are also contemplated herein.

Figure 3:
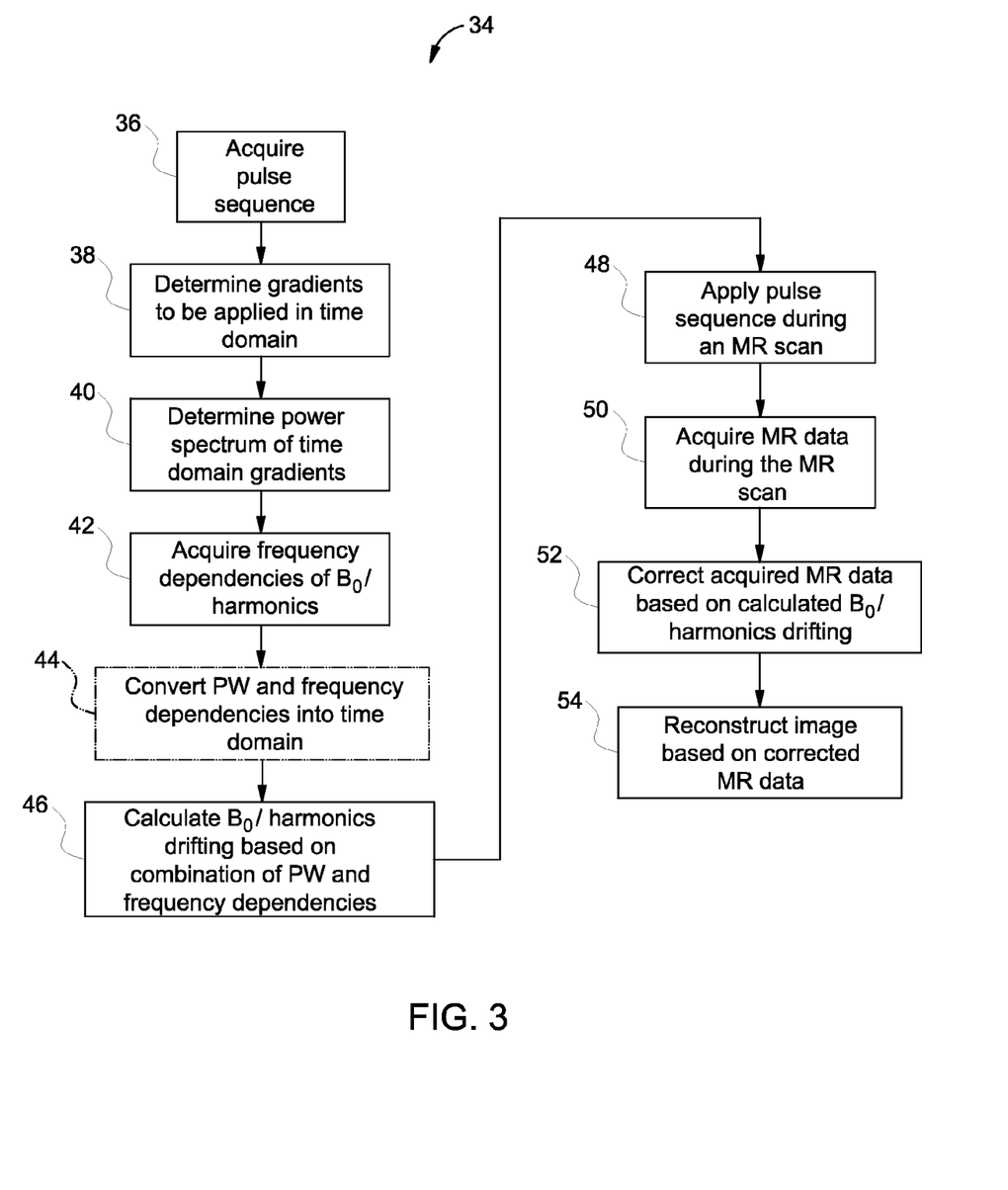
FIG. 3 is a flowchart illustrating a technique for correcting acquired MR data due to magnetic field and/or harmonics drifting according to an embodiment of the invention.

FIG. 3 illustrates a technique 34 for correcting acquired MR data due to magnetic field and/or harmonics drifting according to an embodiment of the invention. Technique 34 includes characterizing magnetic field and/or harmonics drift as a function of frequency. Characterizing the drift begins with acquiring a pulse sequence at block 36. The pulse sequence may be any pulse sequence that includes gradient pulses to be used during imaging. At block 38, the gradients to be applied during the pulse sequence are determined in the time domain. Determining the gradients may include developing a pulse sequence diagram (PSD) based on the entire pulse sequence or based solely on the gradients of the PSD.

Figure 4:
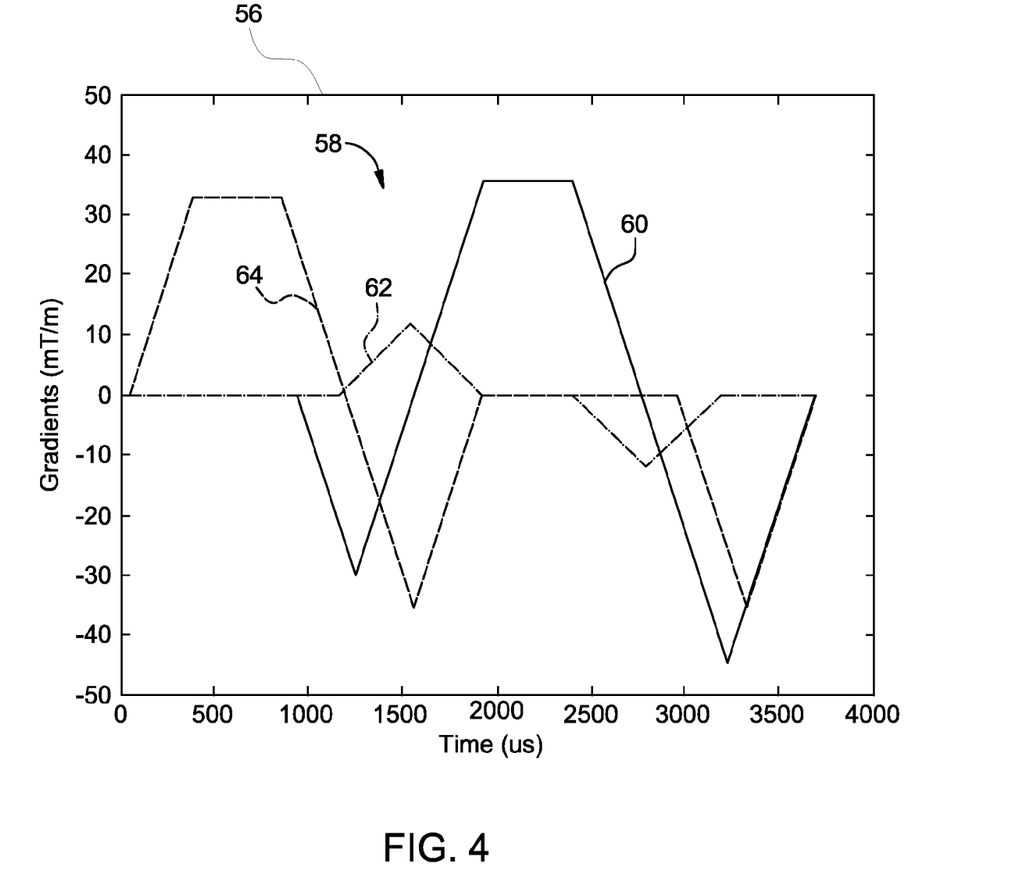
FIG. 4 is a plot showing a pulse sequence diagram according to an embodiment of the invention.

Referring to FIG. 4, a PSD 56 of a pulse sequence is shown. PSD 56 illustrates only gradient pulses 58 to be applied during the pulse sequence. Gradient pulses 58 include a first gradient 60 to be applied in the x-direction, a second gradient 62 to be applied in the y-direction, and a third gradient 64 to be applied in the z-direction.

Figure 5:
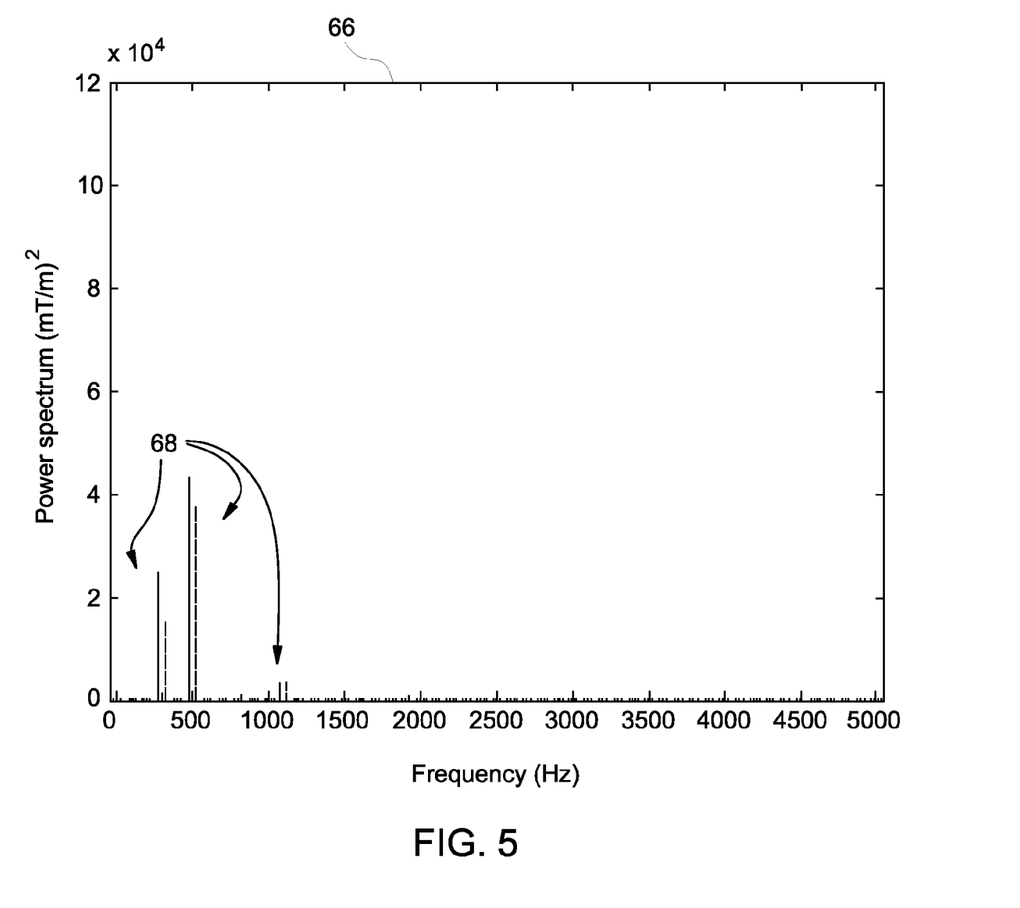
FIG. 5 is a plot of the power spectrum of the pulse sequence diagram of FIG. 4 according to an embodiment of the invention.

Referring back to FIG. 3, the power spectrum (PW) of the time domain gradients is determined at block 40. The PW may be determined from the current input and AC resistance of the gradient at the specific frequency of the PSD as $I(f)^2 R(f)$. FIG. 5 shows a plot 66 of the PW of the gradient pulses 58 of FIG. 4. Based on the frequencies 68 determined, the contribution to $B_0$ and/or harmonics drift can be determined.

Referring again to FIG. 3, the frequency dependencies of the $B_0$ and/or harmonics drift are acquired at block 42. In one embodiment, the frequency dependencies are acquired from a database stored on a computer readable storage medium. As described above, the frequency dependencies include contributions due to passive shim pieces heating, WB heating, and pressure variation.

The calculation of $B_0$ and/or harmonics drifts in technique 34 may be performed in either the frequency domain or in the time domain. Accordingly, if desired to perform the calculation of $B_0$ and/or harmonics drifts in the time domain, technique 34 includes converting determined PW and acquired frequency dependencies of blocks 40, 42 into the time domain at block 44.

Whether in the frequency domain or in the time domain, the $B_0$ and/or harmonics drifts are calculated at block 46 based on a combination of the determined PW and frequency dependencies. For example, the $B_0$ drift may be calculated based on Eqns. 1 or 2 above.

At block 48, the pulse sequence acquired at block 36 is applied during an MR scan, and MR data is acquired during the scan at block 50. The acquired MR data is corrected at block 52 based on the $B_0$ and/or harmonics drifts calculated at block 46. An image having reduced artifacts due to $B_0$ and/or harmonics drifts is reconstructed at block 54 based on the corrected MR data.

Figure 6:
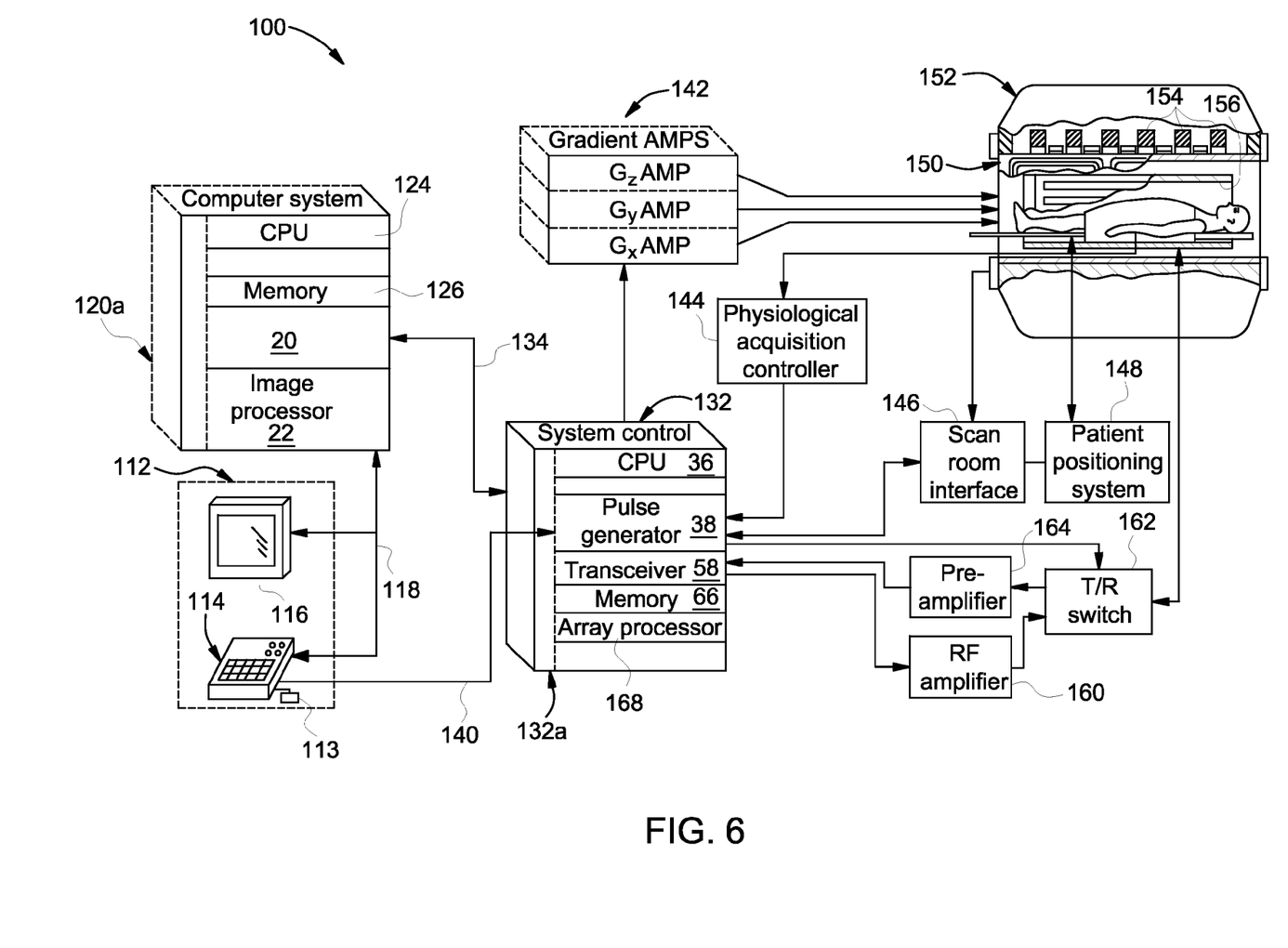
FIG. 6 is a schematic block diagram of an exemplary MR imaging system for use with an embodiment of the invention.

Referring to FIG. 6, the major components of a magnetic resonance imaging (MRI) system 110 incorporating an embodiment of the invention are shown. The operation of the system is controlled for certain functions from an operator console 112 which in this example includes a keyboard or other input device 113, a control panel 114, and a display screen 116. The console 112 communicates through a link 118 with a separate computer system 120 that enables an operator to control the production and display of images on the display screen 116. The computer system 120 includes a number of modules which communicate with each other through a backplane 120a. These modules include an image processor module 122, a CPU module 124 and a memory module 126, known in the art as a frame buffer for storing image data arrays. The computer system 120 communicates with a separate system control 132 through a high speed serial link 134. The input device 113 can include a mouse, joystick, keyboard, track ball, touch activated screen, light wand, voice control, card reader, push-button, or any similar or equivalent input device, and may be used for interactive geometry prescription.

The system control 132 includes a set of modules connected together by a backplane 132a. These include a CPU module 136 and a pulse generator module 138 which connects to the operator console 112 through a serial link 140. It is through link 140 that the system control 132 receives commands from the operator to indicate the scan sequence that is to be performed. The pulse generator module 138 operates the system components to carry out the desired scan sequence and produces data which indicates the timing, strength and shape of the RF pulses produced, and the timing and length of the data acquisition window. The pulse generator module 138 connects to a set of gradient amplifiers 142, to indicate the timing and shape of the gradient pulses that are produced during the scan. The pulse generator module 138 can also receive patient data from a physiological acquisition controller 144 that receives signals from a number of different sensors connected to the patient, such as ECG signals from electrodes attached to the patient. And finally, the pulse generator module 138 connects to a scan room interface circuit 146 which receives signals from various sensors associated with the condition of the patient and the magnet system. It is also through the scan room interface circuit 146 that a patient positioning system 148 receives commands to move the patient to the desired position for the scan.

The gradient waveforms produced by the pulse generator module 138 are applied to the gradient amplifier system 142 having Gx, Gy, and Gz amplifiers. Each gradient amplifier excites a corresponding physical gradient coil in a gradient coil assembly generally designated 150 to produce the magnetic field gradients used for spatially encoding acquired signals. The gradient coil assembly 150 forms part of a resonance assembly 152 which includes a polarizing magnet 154 and a whole-body RF coil 156. A transceiver module 158 in the system control 132 produces pulses which are amplified by an RF amplifier 160 and coupled to the RF coil 156 by a transmit/receive switch 162. The resulting signals emitted by the excited nuclei in the patient may be sensed by the same RF coil 156 and coupled through the transmit/receive switch 162 to a preamplifier 164. The amplified MR signals are demodulated, filtered, and digitized in the receiver section of the transceiver 158. The transmit/receive switch 162 is controlled by a signal from the pulse generator module 138 to electrically connect the RF amplifier 160 to the coil 156 during the transmit mode and to connect the preamplifier 164 to the coil 156 during the receive mode. The transmit/receive switch 162 can also enable a separate RF coil (for example, a surface coil) to be used in either the transmit or receive mode.

The MR signals picked up by the RF coil 156 are digitized by the transceiver module 158 and transferred to a memory module 166 in the system control 132. A scan is complete when an array of raw k-space data has been acquired in the memory module 166. This raw k-space data is rearranged into separate k-space data arrays for each image to be reconstructed, and each of these is input to an array processor 168 which operates to Fourier transform the data into an array of image data. This image data is conveyed through the serial link 134 to the computer system 120 where it is stored in memory. In response to commands received from the operator console 112 or as otherwise directed by the system software, this image data may be archived in long term storage or it may be further processed by the image processor 122 and conveyed to the operator console 112 and presented on the display 116.

A technical contribution for the disclosed method and apparatus is that it provides for a computer implemented system and method for modeling gradient coil operation induced magnetic field drift.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

In accordance with one embodiment of the invention, a magnetic resonance imaging (MRI) apparatus comprises an MRI system and a computer. The MRI system comprises a magnet configured to generate a magnetic field, a plurality of gradient coils, and an RF transceiver system and an RF switch controlled by a pulse module to transmit RF signals to an RF coil assembly to acquire MR images. The computer is programmed to acquire a pulse sequence to be applied during an MR scan and determine a power spectrum of a plurality of gradient pulses of the pulse sequence. The computer is also programmed to calculate a drift of the magnetic field attributable to application of the plurality of gradient pulses by the plurality of gradient coils during application of the pulse sequence and apply the pulse sequence during the MR scan. The computer is further programmed to acquire MR data based on application of the pulse sequence, correct the acquired MR data based on the calculated drift of the magnetic field, and reconstruct an image based on the corrected MR data.

In accordance with another embodiment of the invention, a method comprises determining a power spectrum of a plurality of gradient pulses to be applied in a pulse sequence during an MR scan, determining a magnetic field drift of a main magnetic field due to application of the plurality of gradient pulses during the pulse sequence, and applying the pulse sequence during the MR scan. The method also comprises acquiring MR data based on application of the pulse sequence, correcting the acquired MR data based on the magnetic field drift, and reconstructing an image based on the corrected MR data.

In accordance with another embodiment of the invention, a non-transitory computer readable medium having stored thereon a computer program comprises instructions, which, when executed by a computer, cause the computer to determine a power spectrum of a plurality of gradient pulses to be applied in a pulse sequence during an MR scan and to characterize a dependency of a main magnetic field on at least one frequency of the power spectrum to obtain a main magnetic field drift. The instructions further cause the computer to apply the pulse sequence during the MR scan, acquire MR data based on application of the pulse sequence, correct the acquired MR data based on the main magnetic field drift, and reconstruct an image based on the corrected MR data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A magnetic resonance imaging (MRI) apparatus comprising:
    an MRI system having:
        a magnet configured to generate a magnetic field;
        a plurality of gradient coils; and
        an RF transceiver system and an RF switch controlled by a pulse module to transmit RF signals to an RF coil assembly to acquire MR images; and
    a computer programmed to:
        acquire a pulse sequence to be applied during an MR scan;
        determine a power spectrum of a plurality of gradient pulses of the pulse sequence;
        calculate a drift of the magnetic field attributable to application of the plurality of gradient pulses by the plurality of gradient coils during application of the pulse sequence;
        apply the pulse sequence during the MR scan;
        acquire MR data based on application of the pulse sequence;
        correct the acquired MR data based on the calculated drift of the magnetic field; and
        reconstruct an image based on the corrected MR data.

2. The MRI apparatus of claim 1 wherein the MRI system further comprises a plurality of passive shim pieces positioned adjacently to the plurality of gradient coils; and
    wherein the computer, in being programmed to calculate the drift, is programmed to calculate the drift based on a heating of the passive shim pieces.

3. The MRI apparatus of claim 1 wherein the computer is further programmed to acquire a model of drift frequency dependencies; and
    wherein the computer, in being programmed to calculate the drift, is programmed to calculate the drift based on a at least one frequency of the power spectrum and based on the model of drift frequency dependencies.

4. The MRI apparatus of claim 3 wherein a first component of the model of drift frequency dependencies comprises a contribution due to passive shim pieces heating;
    wherein a second component of the model of drift frequency dependencies comprises a contribution due to warm bore heating; and
    wherein a third component of the model of drift frequency dependencies comprises a contribution due to pressure variation.

5. The MRI apparatus of claim 4 wherein the computer is programmed to determine the first component from a physical model based analytical simulation.

6. The MRI apparatus of claim 4 wherein the computer is programmed to determine the second component from a physical model based analytical simulation.

7. The MRI apparatus of claim 4 wherein the computer is programmed to determine the third component by an experimental measurement.

8. The MRI apparatus of claim 4 wherein a fourth component of the model of drift frequency dependencies comprises a contribution due to a helium temperature change.

9. The MRI apparatus of claim 3 wherein the computer, in being programmed to acquire the model of drift frequency dependencies, is programmed to acquire the model of drift frequency dependencies from a database stored on a computer readable storage medium.

10. The MRI apparatus of claim 1 wherein the computer, in being programmed to calculate the drift, is programmed to calculate a $B_0$ drift.

11. The MRI apparatus of claim 1 wherein the computer, in being programmed to calculate the drift, is programmed to calculate a harmonics drift.

12. The MRI apparatus of claim 1 wherein the computer, in being programmed to calculate the drift, is programmed to calculate the drift in the time domain.

13. A method comprising:
    determining a power spectrum of a plurality of gradient pulses to be applied in a pulse sequence during an MR scan;
    determining a magnetic field drift of a main magnetic field due to application of the plurality of gradient pulses during the pulse sequence;
    applying the pulse sequence during the MR scan;
    acquiring MR data based on application of the pulse sequence;
    correcting the acquired MR data based on the magnetic field drift; and
    reconstructing an image based on the corrected MR data.

14. The method of claim 13 wherein determining the magnetic field drift comprises determining the magnetic field drift based on the equation:

$$B_0^{PSD}(f) = PW(f) \cdot B_0(f),$$

where $B_0^{PSD}$ is the magnetic field drift, PW is the power spectrum, and $B_0$ represents an expression for the frequency dependency of the main magnetic field.

15. The method of claim 14 further comprising determining at least one component of $B_0(f)$ from a physical model based analytical simulation.

16. The method of claim 15 wherein determining the at least one component of $B_0(f)$ comprises determining a first component due to passive shim pieces heating.

17. The method of claim 16 wherein determining the at least one component of $B_0(f)$ comprises determining a second component due to warm bore heating.

18. The method of claim 14 further comprising determining at least one component of $B_0(f)$ based on an experimental measurement.

19. The method of claim 18 wherein determining the at least one component of $B_0(f)$ comprises determining a first component due to pressure variation.

20. A non-transitory computer readable medium having stored thereon a computer program comprising instructions, which, when executed by a computer, cause the computer to:
   determine a power spectrum of a plurality of gradient pulses to be applied in a pulse sequence during an MR scan;
   characterize a dependency of a main magnetic field on at least one frequency of the power spectrum to obtain a main magnetic field drift;
   apply the pulse sequence during the MR scan;
   acquire MR data based on application of the pulse sequence;
   correct the acquired MR data based on the main magnetic field drift; and
   reconstruct an image based on the corrected MR data.

21. The computer readable medium of claim 20 wherein the instructions that cause the computer to characterize the dependency, cause the computer to characterize the dependency based on the at least one frequency and based on a model of drift frequency dependencies.

22. The computer readable medium of claim 21 wherein the instructions that cause the computer to characterize the dependency based on a model of drift frequency dependencies, cause the computer to characterize the dependency based on a contribution due to passive shim pieces heating, on a contribution due to warm bore heating, and on a contribution due to pressure variation.

* * * * *